United States Patent [19] [11] Patent Number: 4,891,515
Jones et al. [45] Date of Patent: Jan. 2, 1990

[54] SOLUTION ANALYZING MASS SPECTROMETER

[75] Inventors: David Jones, Sale; Russel P. Atherton, Timperley; Mark A. McDowall, Atrincham, all of United Kingdom

[73] Assignee: VG Instruments Group Limited, Crawley, United Kingdom

[21] Appl. No.: 151,062

[22] Filed: Feb. 1, 1988

[30] Foreign Application Priority Data

Jan. 30, 1987 [GB] United Kingdom ............... 8702058
Jul. 10, 1987 [GB] United Kingdom ............... 8716252

[51] Int. Cl.$^4$ .................................. D01D 59/44
[52] U.S. Cl. ................................ 250/288; 250/427
[58] Field of Search ............... 250/288, 427, 423 R, 250/288 A, 503, 505.1, 426

[56] References Cited

U.S. PATENT DOCUMENTS 4,164,654 8/1979 Butler et al. ..................... 250/426
4,647,772 3/1987 Lewis et al. ..................... 250/288

FOREIGN PATENT DOCUMENTS 1191520 5/1970 United Kingdom ........... 250/505.1
2146170 4/1985 United Kingdom ............. 250/427

OTHER PUBLICATIONS

W. A. Garland et al., "Relatively Simple Modification of an AEI MS-902 High-Resolution Mass Spectrometer to Permit Chemical Ionization Studies", *Chemical Ins.*, pp. 271-281, 1973.

*Primary Examiner*—Janice A. Howell
*Assistant Examiner*—Michael Aronoff
*Attorney, Agent, or Firm*—Chilton, Alix & Van Kirk

[57] ABSTRACT

A mass spectrometer (1) suitable for the analysis of the eluent of a liquid or supercritical fluid chromatograph is disclosed. In order to maximize the flow rate of fluid which can be accepted into its ionization chamber (13), aperture closing means (13) are provided between an electron or particle source (27) and an entrance aperture (40) into the ionization chamber through which electrons or particles enter the chamber when required to ionize the sample therein. The aperture closing means are operable to close said aperture when such ionization is not required, thereby increasing the maximum flow rate into the ionization chamber. Sample ionization may then be effected by means of a glow discharge in the chamber or by a liquid ionization process such as thermospray ionization.

10 Claims, 2 Drawing Sheets

SOLUTION ANALYZING MASS SPECTROMETER

This invention relates to mass spectrometers adapted for the analysis of solutions of a sample in a liquid or supercritical fluid solvent in which the sample is ionized by (a) particle bombardment or chemical ionization initiated by particle or electron bombardment; or by (b) an electrical discharge and/or a liquid ionization method such as "thermospray" ionization.

Mass spectrometers suitable for the analysis of small amounts of sample contained in a solution, typically the eluent of a liquid or a supercritical fluid chromatograph, are well known. In one such spectrometer, the liquid solution to be analysed is introduced into the ion source of the spectrometer through a strongly heated capillary tube which causes the vaporization of most of the solvent vapour, and ionization of the solute is typically effected either by "thermospray" (see below) ionization or by chemical ionization initiated by electron bombardment. Such a mass spectrometer is described by Garteiz, D. A. and Vestal, M. L. in L. C., 1986, vol 3(4) pp 334–346, and is capable of producing mass spectra from many thermally labile or involatile solutes. It is therefore especially suitable for the analysis of biochemicals.

In another such mass spectrometer, the eluent from a supercritical fluid chromatograph is decompressed and introduced into the ion source of the spectrometer.

The use of a supercritical fluid chromatograph in place of a liquid chromatograph is advantageous under certain conditions because, firstly, the separation efficiency of supercritical fluid chromatography is often very high and, secondly, an efficient interface to the spectrometer can be more easily constructed. A typical supercritical fluid chromatograph-mass spectrometer is described by Smith, R. D, Fjeldsted, J. G, and Lee, M. L, in J. Chromatography, 1982, vol 247, pp 231–243. Ionization of the chromatograph eluent is typically effected by a beam of electrons from a filament disposed outside the ion chamber of the source, but a glow discharge may alternatively be employed, for example as described hereinafter and in our co-pending British Patent application 8716252, filed 10th July 1987.

The "thermospray" ionization process, described by M.L. Vestal in Int. J. Mass Spectrom. and Ion Phys., 1983, vol. 46, pp 193–196, is especially suitable for use with aqueous solutions or with solvents which comprise highly polar organic materials. Ions, frequently clustered with molecules of solvent, are formed directly from evaporating droplets of solution, and these ions exhibit very little fragmentation. However, the efficiency of "thermospray" ionization is low when solvents of low polarity are in use, and an alternative method of ionization for use in these circumstances is desirable. Conventionally, this takes the form of an electron beam generated by a heated filament located outside the source. The electron beam, typcally directed at right angles to the jet of droplets formed in the ion source, causes ionization of the solvent vapour and generates reactant ions. These reactant ions subsequently react with neutral solute molecules and produce, by a chemical ionization process, ions which are characteristic of the solute.

In some cases, another method of ionization, usually a plasma discharge, is incorporated. This is used to supplement the "thermospray" ionization process, and becomes the most important method of ionization in cases where the efficiency of "thermospray" ionization is low (see, for example, Vestal, C. H., Garteiz, D. A., Smit, R, and Blackley, C. R., 33rd Ann. Confr. on Mass Spectrom. and Allied Topics, San Diego, 1985, pp 771-2).

Both thermospray and supercritial fluid chromatograph-mass spectrometers can accept high flows of solution or fluid providing that the thermospray jet or expanded fluid is introduced into an ionization chamber which is substantially sealed from the remainder of the vacuum system of the spectrometer, thereby permitting a substantial pressure differential to be maintained between the interior of the chamber and the spectrometer vacuum system. Typically the pressure in the ionization chamber may lie between 1 and 20 mbar whilst that in vacuum system should be lower than 10-3 mbar. The ionization chamber itself is separately evacuated by a mechanical vacuum pump connected via large bore tubing (typically 1 cm diameter).

In cases where either pure "thermospray" ionization or a discharge ionization is relied on, the ionization chamber is typically completely sealed from the mass spectrometer vacuum system except for the exit orifice for the ions. However, when an electron emitting filament is provided to assist "thermospray" ionization or to permit conventional operation of a supercritical fluid chromatograph-mass spectrometer, it is essential that it is located outside the chamber in the region of low pressure in order to avoid premature failure. Consequently, an additional hole must be provided in the chamber body to allow electrons to enter the chamber. As an alternative to the provision of a filament, ionization may be effected by a beam of neutral atoms or ions which may also enter the ion source through a hole. When used with an external filament, such an ion source closely resembles the directly coupled liquid introduction type of ion source described by Arpino and Guiochon (Anal. Chem., 1979, vol. 51 (7) pp 683A), except that additional heating of the inlet capillary is provided. As explained by Arpino, the flow of solution into a source of this kind is limited to a low value because of the difficulty of maintaining an adequate pressure differential between its interior and the vacuum system when both an electron entrance aperture and an ion exit aperture are provided. In the sources described by Arpino, a cryopumpis installed adjacent to the ion source so that solvent vapour is condensed and frozen on to part of the pump as it leaves the ion source, maintaining a lower pressure in the vacuum system of the spectrometer. However, such a system required regular cleaning and is inconvenient and expensive to operate. It has not been adaped for use with ion sources of the type in question, even when these are fitted with electron emitting filaments, which necessitates the provision of an electron entrance aperture. Consequently, the maximum flow rateof solution or fluid into such sources is limited.

It is the object of the present invention to provide a mass spectrometer capable of ionizing a solution by (a) a particle bomardment or chemical ionization initiated by particle or electron bombardment; or by (b) an electrical discharge and/or a liquid ionization method such as "thermospray" ionization, said spectrometer having an improved solution flow rate acceptance.

In accordance with this objective there is provided a mass spectrometer arranged for analysis of a sample in a fluid solution, said spectrometer comprising a mass analyzer, a sample ion generating means comprising an ionization chamber, and means for heating said fluid solution and expanding it into said chamber, said chamber being provided with an exit aperture through which ions may pass to said mass analyzer, an entrance aperture through which electrons or particles may pass into said chamber to cause ionization of molecules therein, and aperture closing means operable to close said entrance aperture.

In one prefered embodiment of the invention the spectrometer comprised:
(a) a said means for heating said fluid solution and expanding it into said ionization chamber;
(b) means for evacuating said ionization chamber;
(c) a said exit aperture disposed in a wall of said ionzation chamber through which ions present in said ionization chamber may pass to said mass analyzer;
(d) a said entrance aperture disposed in a wall of slid ionization chamber through which electrons or particles (e.g. neutral atoms, or ions) may enter said ionization chamber and cause ionization of at least some of the molecules present in said ionization chamber; and
(e) a said aperture closing means disposed adjacent said entrance aperture and operable to close said entrance aperture when ionization due to said electrons or particles is not required.

In another preferred embodiment the mass spectrometer is arranged for the analysis of a sample dissolved in a liquid solution and comprises:
(a) means for heating a said liquid solution and expanding it through a spraying means adapted to spray into said ionization chamber a most comprising solvent vapour and droplets comprising molecules of said sample;
(b) means for evacuating said ionization chamber;
(c) a said exit aperture disposed in a wall of said chamber through which ions present in said chamber may pass to said mass analyzer;
(d) a said entrance aperture disposed in a wall of said chamber through which electrons or particles (e.g. neutral atoms, or ions) may enter said chamber and cause ionization of at least some of the molcules present in said chamber; and
(e) a said aperture closing means disposed adjacent said entrance aperture and operable to close sad entrance aperture when ionization due to said electrons or particles is not required.

In another preferred embodiment the mass spectrometer is arranged for the analysis of a sample dissolved in the eluent from a supercritical fluid chromatograph and comprises:
(a) means for heating a said eluent and expanding it into said ionization chamber;
(b) means for evacuating said ionization chamber;
(c) a said exitaperture disposed in a wall of said ionization chamber through which ions present in said chamber may pass into a mass analyser;
(d) a said entrance aperture disposed in a wall of said chamber through which electrons or particles (e.g. neutral atoms or ions) may enter said ionization chamber and cause ionization of at least some of themolecules present in said ionization chamber; and
(e) a said aperture closing means disposed adjacent said entrance aperture and operable to close said entrance aperture when ionization due to said electrons or particles is not required.

In the spectrometer of the invention the aperture closing means preferably is provided with actuating means which operate to close or to open the entrance aperture, for example by moving the closing means to cover or uncover the aperture.

The spectrometer of the invention preferably also comprises an electronor particle generating means, e.g. means for generating a beam of electrons, ions or neutral atoms Thus for example where the ionizing particles are electrons these may be emitted by a heated filament disposed outside the ionization chamber, and the entrance aperture may comprise a slit in a wall of the chamber. Where ionization by the electrons or particles is not required, for example when either thermospray or discharge ionization is in use, the entrance aperture required to admit electrons, or other particles such as neutral atoms or ions, into the ionization chamber may be closed. As this aperture is conventionally larger than the exit aperture through which ions leave, closing it substantially reduces the rate of escape of solvent or fluid vapour from the chamber into the mass spectrometer vacuum system and permits the use of a higher flow rate of liquid solution or fluid.

The inventors have found that in prior thermospray mass spectrometers equipped with the additional entrance aperture, the solution slow rate is most restricted in the case of solutions containing a high proportion of water. It has also been found that in general, electron impact initiated chemical ionization or particle bombardment ionization is not required with such solutions because the efficiency of "thermospray" ionization appears to be highest with aqueous solutions. Consequently, advantage is to be had by closing the entrance aperture when "thermospray" ionization alone is adequate, thereby allowing the flow rate of solution to be increased without the use of a cryopump.

Similarly, in the case of a supercritical fluid mass spectrometer, greater flows of fluid can be admitted into the ion source when the aperture is closed according to the invention and ionization is effected without the use of an electron beam or any other particles generated outside the ionization chamber.

In a still further preferred embodiment, electrode means are provided in the ionization chamber so that a glow discharge can be established in the chamber on application of a suitabLe electrical potential to the electrode means. Preferably, but not essentially, the electrode means constitutes the means for expanding the fluid solution, which is electrically insulated from the wall of the ionization chamber. A suitable electrical potential is applied between the means for expanding the fluid solution and the wall of the ionization chamber, thereby generating a glow discharge which causes ionization of the sample molecules. Use of discharge ionization processes of this kind are described in European patent publication number 252758, and our copending UK Patent application number 8716252 filed on the 10th July 1987. Alternatively, a separate electrode may be provided, as suggested for the thermospray source by Vestal, C. H. Garteiz, D. A., Smit, R, and Blackley, C. R., 33rd Ann. Confr. on Mass Spectrom. and Allied Topics, May 1985, (San Diego, U.S.A.) pp 771-2.

The glow discharge ionization process so provided is used in the invention in cases where either supercritical fluid chromatography is employed or where adequate ionization cannot be obtained by "thermospray" ionization alone. Consequently, this feature of the invention allows the use of a higher flow rate of fluid or on-aqueous solutions than is possible with conventional spectrometers, whilst still allowing ionization using a heated filament with lower flow rates when required.

Preferably the aperture closing means comprises a sliding member provided with a hole which serves to define the effective size of the entrance aperture. The sliding member is located adjacent to a larger aperture in the wall of the ionization chamber and is capable of being positioned so that the aperture is aligned with the hole, or with a solid part of the sliding member closing the aperture. The sliding member is preferably operated by means of a flexible bowden cable attached to an actuator mounted on the vacuum enclosure of the spectrometer. The actuator may be operated be operater manually or electrically in response to a signal from a computer conventionally used to control the spectrometer.

An embodiment of the invention will now be described in greater detail by way of example and with reference to the following figures, in which.

Figure 1:
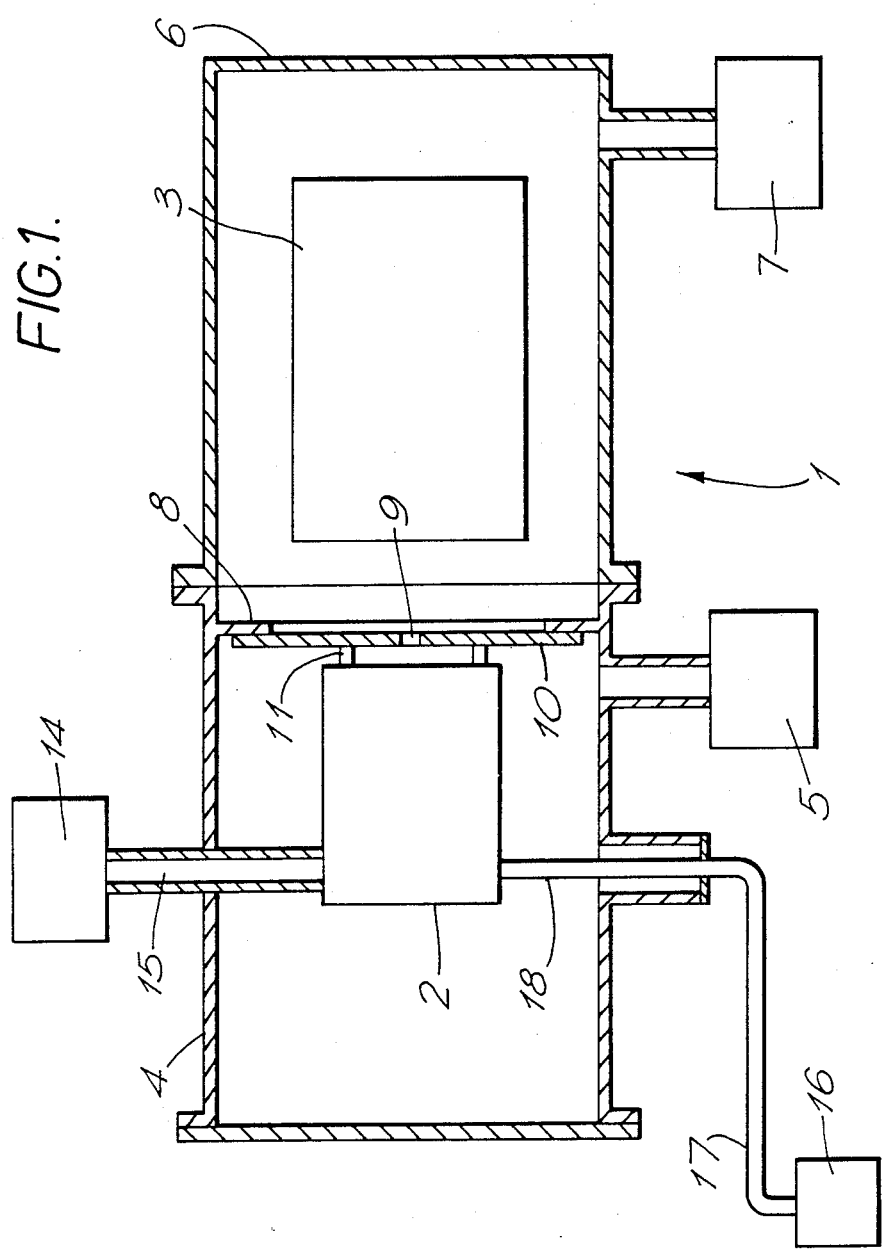
FIG. 1 illustrates a mass spectrometer according to the invention.

Referring first to FIG. 1 in which the mass spectrometer 1 is shows schematically, the spectrometer comprises an ion source 2 and a mass analyser 3 contained in vacuum housings 4 and 6, respectively. High vacuum pumps 5 and 7 are provided to evacuate housings 4 and 6, as shown. Mass analyser 3 is typically a conventional quadrupole analyser and incorporates an ion detector (not shown). Housings 4 and 6 are separated by diaphragm 8 which supports a mounting flange 10 containing a small aperture 9 through which ions pass from source 2 into analyser 3. Aperture 9 is small enough to allow the pressure in housing 6 to be maintained at a value about ten times lower than that in housing 4. Source 2 is supported from flange 10 by insulated supports 11.

Figure 2:
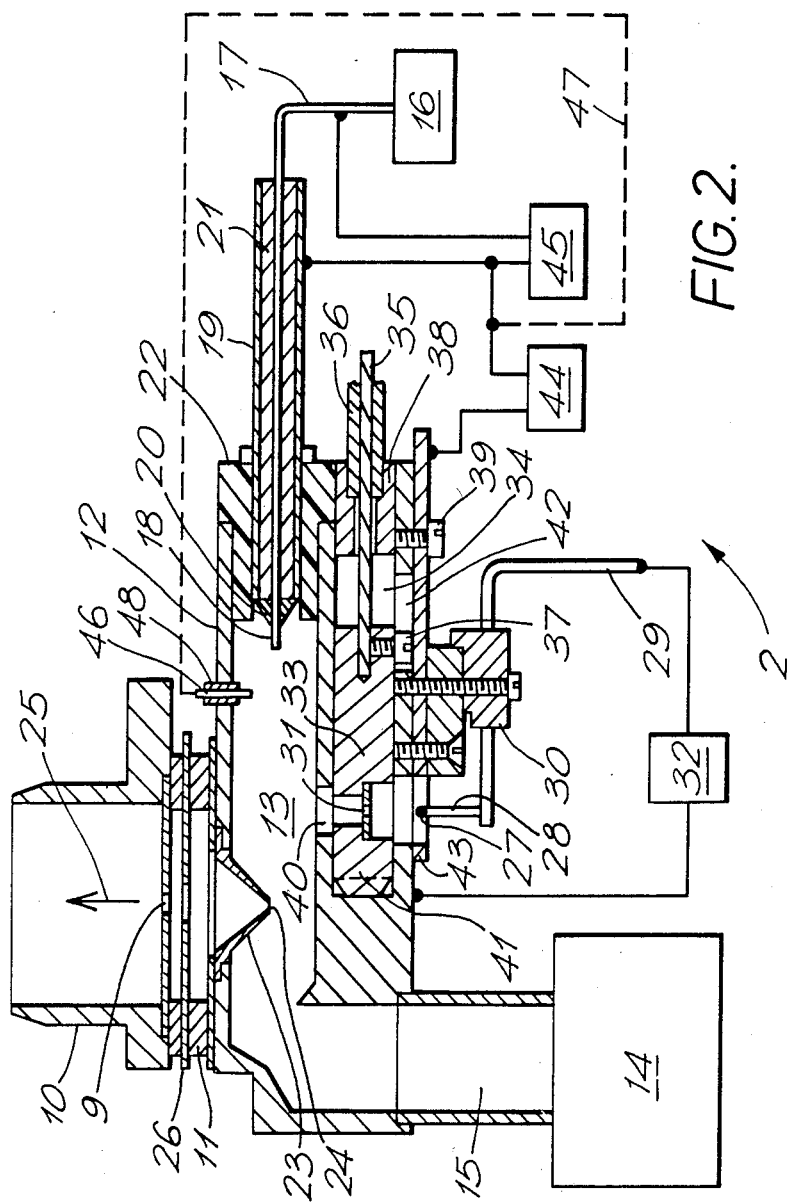
FIG. 2 illustrates in greater detail part of the spectrometer of FIG. 1.

Referring next to FIG. 2, ion source 2 comprises a source body 12 which encloses an ionization chamber 13. A vacuum pump 14 evacuates chamber 13 through a large bore pipe 15. Pipe 15 may incorporate an electrically insulating section so that body 12 can be maintained at a potential different from that of housing 4.

The solution (liquid or supercritical fluid) to be analysed is pumped by apump 16 (which is typically part of a liquid or supercritical fluid chromatograph) through a narrow bore connecting pipe 17 into a heated nozzle 18, which conveniently comprises the end of pipe 17, suitably prepared. Pipe 17 may also comprise an electrically insulated section so that pump 16 and body 12 may be operated at different potentials. Heated nozzle 18 is coaxially located in a probe 19 and is brazed or welded to a plug 20 which is also welded into the end of probe 19. An insulating tube 21 prevents accidental electrical contact between tube 17 and probe 19, and nozzle 18 is heated by passing an electrical current from a supply 45 through pipe 17, plug 20 and probe 19 as shown.

Probe 19 is adapted to make a substantially vacuum tight seal with an insulating bush 22 (typically PTFE or Vespel) fitted in body 12. Preferably probe 19 is further adapted to fit a conventional vacuum insertion lock (not shown) mounted on housing 4, so that it can be removed when not required and replaced by a sample introduction probe.

In the case of a thermospray ion source, nozzle 18 comprises a spraying means adapted to produce a jet of droplets in chamber 13 in the manner of a conventional thermospray ion sources and the vapour resulting from the evaporation of thesolvent is removed by pump 14. An extractor cone 23, positioned in the wall of body 12, contains a small orifice 24 in its apex, through which ions exit from chamber 13 in the direction of arrow 25 into mass analyser 3. An electrode 26, to which a suitable electrical potential is applied, is adapted to focus ions massing through orifice 24 into mass analyser 3.

In the case of a supercritical fluid chromatography-mass spectrometer, pipe 17 and nozzle 18 are adapted in a conventional way to decompress the fluid in as small a distance as possible thereby avoiding a phase change in the decompression process which is known to cause poor performance.

In order to provide for electron impact initiated chemical ionization of molecules in chamber 13, a filament 27 is mounted between two filament supports 28 which are in turn attached to two rods 29 moulded in a ceramic block 30. Block 30 is in turn attached by a screw to a mounting plate 43 secured by further screws to body 12. Electrical current is passed through filament 27 via supports 28 and rods 29 so that electrons are emitted. Some of these electrons pass through an electron entrance aperture 31 and a hole 40 (in body 12) into chamber 13. A suitable potential difference (typically u to several hundred volts) is maintained between filament 27 and body 12 by means of a power supply 32 so that the electrons entering chamber 13 have sufficient energy to ionize solvent or fluid molecules in the ionization chamber by electron impact. The resultant ions collide with molecules of sample present in chamber 13 and cause ionization of the sample molecules by a chemical ionization process, as in the case of a conventional direct liquid-introduction mass spectrometer. Alternatively, if the pressure in the ionization chamber is sufficiently low, ionization of the sample molecules may take plate directly by the electrons.

Electron entrance aperture 31 is mounted in a counterbored hole in cylindrical plunger 33 which is slidably located in a bore 34 in body 12. The inner wire 35 of a flexible bowden cable 36 is secured into a hole in the end of plunger 33 by a screw 37, and the outer part of cable 36 is brazed into a bush 38 which is secured in body 12 y screw 39. The end of cable 36 remote from the ion source is connected to a suitable vacuum-tight actuator (not shown) mounted on housing 4. This actuator is adapted to move inner wire 35 between two positions, in one of which aperture 31 is positioned as shown in FIG. 2 to allow electrons to enter chamber 13, and in the other of which hole 40 is substantially closed by a solid portion 41 of plunger 33. The depth of bore 34 is such that when plunger 33 is fully inserted, aperture 31 is correctly located in alignment with filament 27 and hole 40. Plunger 33 is prevented from rotating by means of the head of screw 37 which is located in a slot cut in body 12. In order to minimize the risk of plunger 33 jamming in bore 34, plunger 33 is silver plated and bore 34 is highly polished.

In this way, the electron entrance aperture in source body 12 can be closed when filament 27 is not in use simply by operating the actuator from outside the spectrometer vacuum enclosure, thereby substantially reducing the flow of solvent vapour or fluid from chamber 13 into housing 4 and permitting a higher flow rate of solution to be used. As explained, in the case of a thermospray source, this is chiefly advantageous when a high flow rate of an aqueous solution is to be introduced, under which conditions the need for filament 27 is reduced whilst simultaneously the increase in pressure in housing 4 is potentially the highest.

In order to make use of the discharge ionization process described above, a suitable electrical potential from a power supply 44 may be applied between nozzle 18 and body 12 so that a glow discharge is formed in the vapour present in spraying chamber 13. In the case of thermospray sources this discharge provides another method of ionization which can assist (or replace) the thermospray ionization process. It is especially useful in cases where the flow rate of a non-aqueous solution into source 2 is so high that it is necessary to close the electron entrance aperture to maintain the pressure in housing 4 at an acceptable In some such cases, "thermospray" ionization alone may be insufficient and the glow discharge can be used to supplement it.

In the case of a supercritial fluid chromatograph mass spectrometer, the discharge may be used to provide ionization according to our copending British patent application No. 8716252 so that no additional ionization by electrons or other particles is required.

It will be appreciated that it is not essential that pipe 17 and nozzle 18 be used as one of the electrodes for the discharge in either the thermospray or supercritical fluid chromatograph cases. An additional electrode 46 mounted through insulating bush 48 may be provided and supply 44 may be connected via lead 47 to electrode 46 rather than suppy 45 and tube 19.

We claim:

1. A mass spectrometer arranged for analysis of a sample in a fluid solution, said spectrometer comprising a mass analyzer, a sample ion generating means comprising an ionization chamber, and means for heating said fluid solution and expanding it into said chamber, said chamber being provided with an exit aperture through which ions may pass to said mass analyzer, an entrance aperture through which electrons or particles may pass into said chamber to cause ionization of molecules therein, and aperture closing means operable to close said entrance aperture.

2. A spectrometer as claimed in claim 1 comprising
   (a) a said means for heating a said fluid solution and expanding it into said ionization chamber;
   (b) means for evacuating said ionization chamber;
   (c) a said exit aperture disposed in a wall of said ionization chamber through which ions present in said ionization chamber may pass to said mass analyzer;
   (d) a said entrance aperture disposed in a wall of said ionization chamber through which particles may enter said ionization chamber and cause ionization of at least some of the molecules present in said ionization chamber; and
   (e) a said aperture closing means disposed adjacent said entrance aperture and operable to close said entrance aperture when ionization due to said electrons or particles is not required.

3. A spectrometer as claimed in claim 1 arranged for the analysis of a sample in a liquid solution, said spectrometer comprising:
   (a) means for heating a said liquid solution and expanding it through a spraying means adapted to spray into said ionization chamber a mist comprising solvent vapour and droplets comprising molecules of said sample;
   (b) means for evacuating said ionization chamber;
   (c) a said exit aperture disposed in a wall of said chamber through which ions present in said chamber may pass into said mass analyzer;
   (d) a said entrance aperture disposed in a wall of said chamber through which electrons or particles may enter said chamber and cause ionization of at least some of the molecules present in said chamber; and
   (e) a said aperture closing means disposed adjacent said entrance aperture and operable to close said entrance aperture when ionization due to said electrons or particles is not required.

4. A spectrometer as claimed in claim 1 arranged for the analysis of a sample dissolved in the eluent from a supercritical fluid chromatograph, said spectrometer comprising:
   (a) means for heating a said eluent and expanding it into said ionization chamber;
   (b) means for evacuating said ionization chamber;
   (c) a said exit aperture disposed in a wall of said ionization chamber through which ions present in said chamber may pass to said mass analyzer;
   (d) a said entrance aperture disposed in a wall of said chamber through which electrons or particles may enter said ionization chamber and cause ionization of at least some of the molecules present in said ionization chamber; and
   (e) a said aperture closing means disposed adjacent said entrance aperture and operable to close said entrance aperture when ionization due to said electrons or particles is not required.

5. A spectrometer as claimed in claim 1 further comprising a means for generating said electrons or particles, said means for generating being arranged outside of said ionization chamber.

6. A spectrometer as claimed in claim 5 wherein said means for generating comprises a heatable filament and wherein said entrance aperture comprises a slit arranged to permit electrons emitted from said filament to enter said chamber.

7. A spectrometer as claimed in claim 1 in which electrode means are provided in said ionization chamber for establishing a glow discharge therein whereby to ionize molecules present in said ionization chamber.

8. A spectrometer as claimed in claim 7 in which said electrode means constitutes said means for expanding a said fluid solution into said ionization chamber.

9. A spectrometer as claimed in claim 1 wherein said aperture closing means comprises a sliding member having a hole herein and disposed adjacent to the wall of the said ionization chamber in which said entrance aperture is formed, said sliding member being movable between a first position in which said entrance aperture is substantially closed by said sliding member and a second position in which said entrance aperture is aligned with said hole and wherein said aperture closing means is provided with actuating means operable to move said sliding member between said positions.

10. A spectrometer as claimed in claim 9 wherein said sliding member is disposed between said wall of said ionization chamber and a filament arranged to emit electrons, and wherein said hole in said sliding member adjacent said wall is smaller than said entrance aperture in said wall adjacent said sliding member.

* * * * *